United States Patent
Cincotta et al.

(10) Patent No.: US 9,645,552 B2
(45) Date of Patent: *May 9, 2017

(54) TIME VALIDATION INDICATOR

(71) Applicant: Performance Indicator, LLC, Lowell, MA (US)

(72) Inventors: Louis Cincotta, Andover, MA (US); Clifford Parker, New Ipswich, NH (US); Satish Agrawal, Concord, MA (US)

(73) Assignee: PERFORMACE INDICATOR, LLC, Lowell, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/059,866

(22) Filed: Mar. 3, 2016

(65) Prior Publication Data

US 2016/0187855 A1    Jun. 30, 2016

Related U.S. Application Data

(63) Continuation of application No. 13/916,617, filed on Jun. 13, 2013, now Pat. No. 9,310,311.

(51) Int. Cl.
*G04F 1/00* (2006.01)
*G04F 1/02* (2006.01)
(Continued)

(52) U.S. Cl.
CPC .............. *G04F 1/02* (2013.01); *C09D 11/50* (2013.01); *G01N 21/78* (2013.01); *G01N 31/229* (2013.01);
(Continued)

(58) Field of Classification Search
CPC ....................................................... G04F 1/00
See application file for complete search history.

(56) References Cited

U.S. PATENT DOCUMENTS 3,018,611 A   1/1962  Biritz
3,480,402 A   11/1969 Jackson
(Continued)

FOREIGN PATENT DOCUMENTS

| JP | 11316292 | 11/1999 |
|----|----------|---------|
| WO | 2006091464 | 8/2006 |
| WO | 2006091465 | 8/2006 |

OTHER PUBLICATIONS

Takashi Horiguchi, et al., "Reversible coloring/decoloring reaction of leuco dye controlled by long-chain molecule" Thin Solid Films, 2008, 2591-94, vol. 516.
(Continued)

*Primary Examiner* — Amy Cohen Johnson
*Assistant Examiner* — Jason Collins
(74) *Attorney, Agent, or Firm* — Morgan, Lewis & Bockius LLP

(57) ABSTRACT

A time validation indicator is disclosed comprising at least a receiving layer and an activating layer. The receiving layer comprises at least one or more masking colorants and one or more deactivators that cause and maintain the one or more masking colorants in an initial colored state. The activating layer comprises at least one or more migratory activators that migrate into the receiving layer upon at least a portion of the receiving layer being placed in contact with at least a portion of the activating layer to initiate a predetermined time period. The migration of the one or more migratory activators into the receiving layer causes at least a portion of the one or more masking colorants to advance to a final colorless state resulting in a visual color change of the receiving layer that indicates the predetermined time period has elapsed. Also disclosed are methods for creating and using the inventive time validation indicator.

53 Claims, 9 Drawing Sheets

(51) Int. Cl.
*C09D 11/50* (2014.01)
*G01N 31/22* (2006.01)
*G01N 21/78* (2006.01)
*G04F 13/02* (2006.01)

(52) U.S. Cl.
CPC .............. *G04F 1/00* (2013.01); *G04F 13/02* (2013.01); *Y10T 156/10* (2015.01)

(56) References Cited

U.S. PATENT DOCUMENTS

| | | | |
|---|---|---|---|
| 3,942,467 A | 3/1976 | Witonsky | |
| 3,954,011 A | 5/1976 | Manske | |
| 3,962,920 A | 6/1976 | Manske | |
| 4,212,153 A | 7/1980 | Kydonieus et al. | |
| 4,229,813 A | 10/1980 | Lilly et al. | |
| 4,248,597 A | 2/1981 | McNeely | |
| 4,407,960 A | 10/1983 | Tratnyek | |
| 4,643,122 A | 2/1987 | Seybold | |
| 4,812,053 A | 3/1989 | Bhattacharjee | |
| 4,824,827 A | 4/1989 | Kelly et al. | |
| 4,846,095 A * | 7/1989 | Emslander | G01K 11/06 116/206 |
| 4,903,254 A | 2/1990 | Haas | |
| 4,917,503 A | 4/1990 | Bhattacharjee | |
| 5,045,283 A | 9/1991 | Patel | |
| 5,053,339 A | 10/1991 | Patel | |
| 5,058,088 A | 10/1991 | Haas et al. | |
| 5,085,802 A | 2/1992 | Jalinski | |
| 5,446,705 A | 8/1995 | Haas et al. | |
| 5,602,804 A * | 2/1997 | Haas | G01K 3/04 116/206 |
| 5,633,835 A | 5/1997 | Haas et al. | |
| 5,633,836 A | 5/1997 | Langer et al. | |
| 5,667,303 A * | 9/1997 | Arens | G01K 3/04 116/219 |
| 5,822,280 A | 10/1998 | Haas | |
| 5,930,206 A | 7/1999 | Haas et al. | |
| 6,244,208 B1 * | 6/2001 | Qiu | G01K 3/04 116/207 |
| 6,270,122 B1 * | 8/2001 | Shadle | B44C 1/145 116/206 |
| 6,295,252 B1 | 9/2001 | Holt et al. | |
| 6,452,873 B1 | 9/2002 | Holt et al. | |
| 6,973,894 B1 | 12/2005 | Adamy et al. | |
| 7,139,226 B2 | 11/2006 | Haas et al. | |
| 7,254,095 B1 * | 8/2007 | Braunberger | G04F 13/04 368/327 |
| 7,742,367 B2 | 6/2010 | Haas | |
| 7,791,984 B2 | 9/2010 | Su et al. | |
| 7,807,075 B2 | 10/2010 | Evans et al. | |
| 7,898,907 B1 | 3/2011 | Holt et al. | |
| 7,974,157 B2 * | 7/2011 | Su | G01N 31/229 116/206 |
| 8,014,234 B2 * | 9/2011 | Braunberger | G04F 13/04 368/327 |
| 8,088,479 B2 | 1/2012 | Su et al. | |
| 2003/0053377 A1 * | 3/2003 | Spevacek | G01K 3/04 368/327 |
| 2003/0166467 A1 * | 9/2003 | Azuma | B41M 5/465 503/217 |
| 2005/0286350 A1 * | 12/2005 | Wien | G04F 13/06 368/327 |
| 2008/0145948 A1 | 6/2008 | Menon | |
| 2009/0093063 A1 * | 4/2009 | Anslyn | A61K 8/11 436/164 |
| 2009/0176673 A1 * | 7/2009 | Hanes | A61K 8/498 510/100 |
| 2010/0012018 A1 * | 1/2010 | Ribi | C09B 57/10 116/207 |
| 2011/0144603 A1 | 6/2011 | Song | |
| 2012/0143160 A1 * | 6/2012 | Song | G01N 21/78 604/361 |
| 2012/0165336 A1 * | 6/2012 | Steiner | A61J 1/035 514/249 |
| 2012/0238446 A1 * | 9/2012 | Tsuchimura | B41M 5/305 503/207 |
| 2012/0266806 A1 * | 10/2012 | Ribi | C09B 57/10 116/206 |

OTHER PUBLICATIONS

Richard A. Evans, et al., "The generic enhancement of photochromic dye switching speeds in a rigid polymer matrix", Nature Materials, 2005, 249-53, vol. 4-issue 3.
T.M. Goulding, "Pressure-Sensitive Adhesives", Handbook of Adhesive Technology 2nd Edition, 2003, chapter 44.
The International Search Report for International Application No. PCT/US2014/040595, dated Oct. 1, 2014, 3 pages.
The International Written Opinion for International Application No. PCT/US2014/040595, dated Oct. 1, 2014, 16 pages.
The International Preliminary Report on Patentability, dated Oct. 29, 2015, 18 pages.

* cited by examiner

TIME VALIDATION INDICATOR

CROSS-REFERENCE TO RELATED APPLICATION

This application is a continuation application of U.S. application Ser. No. 13/916,617 filed on Jun. 13, 2013 and entitled "Time Validation Indicator," which is hereby incorporated by reference in its entirety.

BACKGROUND OF THE INVENTION

These teachings relate generally to time validation indicators, and more particularly, to the preparation and use of time validation indicators that are easily adaptable for various time intervals of expiration, and hence capable of providing digital and distinct indication of expiration of a predetermined time period.

Various indicators have been utilized in a number of different applications for indicating when a specific time period has elapsed. For example, time-temperature indicators have been used in areas such as pharmaceutical and food industries for indicating when perishable materials, i.e. materials having a measurable shelf-life, reach a predetermined expiration date and need to be discarded. Other examples of areas for which time indicators have been utilized include general inventory management, monitoring projects and activities, security badges, and a host of other time dependent events.

Currently, the majority of known time indicators provide, after activation, a visual indication of a predetermined period of time. Many of these known time indicators provide this visual indication by way of color change through the use of dye migration or dye diffusion. For example, U.S. Pat. Nos. 4,903,254, 5,822,280, and 7,139,226 employ the use of colored indicators that migrate, once activated, through opaque films to indicate the passage of time. In these systems, the final colored state of the indicator is generated in or below the opaque layer and then migrates through this layer to become visible. Alternative efforts, such as those cited U.S. Pat. Nos. 4,212,153, 4,248,597, and 4,643,122 describe similar approaches that include the migration of an acid/base or solvent within a laminated structure containing a pH indicator, such that a color change results following activation due to a subsequent change in pH. Other known time indicators provide a color change by way of chemical reactions, such as those cited in U.S. Pat. Nos. 3,018,611 and 4,812,053 which employ an oxygen reactive material that reacts with oxygen upon exposure and produces a visual color change. Furthermore, U.S. Pat. No. 5,085,802 describes an additional color change reaction suitable for providing a visual indication of a predetermined period of time. This color change reaction involves the generation of an acid/base "in-situ" through the use of enzymes in the presence of a pH indicator, thereby producing a subsequent color change with a change in pH.

A general problem that exists with approaches based on dye migration or dye diffusion, as well as chemical reactions, to provide a visual indication of a predetermined time period is the gradual nature of the color change over the time period, thereby making it difficult for the user to ascertain exactly when the designated end point is reached. A common approach in addressing the foregoing problem is by additionally incorporating the use of a control color strip or target strip adjacent to the time indicator in order to make visual comparisons as time progresses. However, the use of color or target strips add to the cost of making and employing the time indicators, as well as still having the possibility of user error in determining when the predetermined time period has elapsed. Time indicators that rely solely on the migration of dyes, solvents, reactants, etc. cannot escape the grey scale problem since it is an inherent aspect of diffusion kinetics. Another drawback includes the inability to use such time indicators for long time periods, i.e. month(s) or year(s). Therefore, there is a continued need to develop reliable, visual time indicator systems and devices which can be used for a variety of different applications and predetermined time periods.

There have been further attempts in providing a visual indication of a predetermined period of time with the migration of jelly or liquids through a wick material to indicate the lapse or elapse of time, such as those cited in U.S. Pat. Nos. 3,954,011 and 3,962,920. These technologies impregnate the wicking material with an indicator and the progress of a fluid along the wick material is visibly indicated and used to measure or determine a lapse or elapse of time. One drawback to such approaches is that they generally require a reservoir of fluid that is needed in order to visually indicate or measure a passage of time. Such a requirement increases the cost of utilizing these types of approaches, as well as limits their applicability, etc.

Given the drawbacks of the current time indicators utilized to provide a visual indicator of a predetermined period of time, there is, therefore, a need for a time validation indicator that is capable of providing a digital (step-wise) and distinct indication when a predetermined time period has elapsed. In providing a digital and distinct indication, such a time validation indicator affords a more reliable and accurate visual indication than that of the prior art. It is also desirable, therefore, to provide a time validation indicator that is easily adaptable for use in determining expiration of a wide variety of time intervals, i.e. short or longer periods of time, resulting in more applicability. Furthermore, it also desirable to provide a time validation indicator that is inexpensive and simpler to construct and to employ than that of the prior art.

BRIEF SUMMARY OF THE INVENTION

The present teachings provide for a time validation indicator comprising a receiving layer and an activating layer. The receiving layer comprises one or more masking colorants and one or more deactivators that cause and maintain the one or more masking colorants in an initial colored state. In some instances, the receiving layer may further comprise one or more polymers that function together with the one or more deactivators to cause and maintain the one or more masking colorants to be in the initial colored state. The activating layer comprises one or more migratory activators that migrate into the receiving layer upon at least a portion of the receiving layer being placed in contact with at least a portion of the activating layer to initiate a predetermined time period. The migration of the one or more migratory activators into the receiving layer causes at least a portion of the one or more masking colorants to advance to a final colorless state resulting in a visual color change of the receiving layer that indicates the predetermined time period has elapsed. In some instances, the one or more masking colorants may be one or more leuco dyes. In other instances, the one or more deactivators may be one or more electron accepting compounds. In further instances, the one or more migratory activators may be one or more polyoxygenated compounds. In certain constructions, at least one of the receiving layer or the activating layer may further comprise one or more plasticizers that aid in the migration of the one or more migratory activators into the receiving layer. In other constructions, at least one of the receiving layer or the activating layer may also comprise at least one of one or more dispersants, one or more thickeners, one or more wetting agents, or one or more defoamers. In other aspects, at least one of the receiving layer or the activating layer may further comprise one or more adhesive materials that bond together at least a portion of the receiving layer to at least a portion of the activating layer when placed in contact. In further instances, at least one of the activating layer or the receiving layer may also comprise one or more static colorants that are capable of being visually observed upon at least a portion of the one or more masking colorants of the receiving layer being partially or fully in the final colorless state. The time validation indicator of the present teachings may additionally comprise an adhesive layer that bonds together at least a portion of the receiving layer to at least a portion of the activating layer when placed in contact. The time validation indicator of the present teachings may also comprise a colorant layer that comprises one or more static colorants that are capable of being visually observed upon at least a portion of the one or more masking colorants of the receiving layer being partially or fully in the final colorless state. The time validation indicator of the present teachings may further comprise a timing layer that at least partially retards the rate of migration of the one or more migratory activators into the receiving layer. The time validation indicator of the present teachings may optionally comprise one or more base substrates. In some instances, one of the one or more base substrates may include an indicia area that is capable of being visually observed upon at least a portion of the one or more masking colorants of the receiving layer being partially or fully in the final colorless state.

The present teachings also provide for a method for fabricating a time validation indicator. The method of the present teachings comprises forming a receiving layer that comprises one or more masking colorants and one or more deactivators that cause and maintain the one or more masking colorants to be in an initial colored state. In some instances, the receiving layer may further comprise one or more polymers that function together with the one or more deactivators to cause and maintain the one or more masking colorants to be in the initial colored state. The method of the present teachings further comprises forming an activating layer that comprises one or more migratory activators that migrate into the receiving layer upon at least a portion of the receiving layer being placed in contact with at least a portion of the activating layer to initiate a predetermined time period. The method of the present teachings further comprises placing at least a portion of the receiving layer in contact with at least a portion of the activating layer to initiate the predetermined time period and the migration of the one or more migratory activators into the receiving layer. The migration of the one or more migratory activators into the receiving layer causes at least a portion of the one or more masking colorants to advance to a final colorless state resulting in a visual color change of the receiving layer that indicates the predetermined time period has elapsed. In other instances, at least one of the activating layer or the receiving layer may further comprise one or more static colorants that are capable of being visually observed upon at least a portion of the one or more masking colorants of the receiving layer being partially or fully in the final colorless state. The method of the present teachings may further comprise applying an adhesive means that bonds together at least a portion of the receiving layer to at least a portion of the activating layer when placed in contact. The applying of the adhesive means may include rendering an adhesive layer onto at least a portion of at least one of the receiving layer or the activating layer. Alternatively, or in addition, applying the adhesive means may comprise incorporating one or more adhesive materials into at least one of the receiving layer or the activating layer. The method of the present teachings may also include rendering a colorant layer disposed onto at least a portion of the activating layer, in which the colorant layer comprises one or more static colorants that are capable of being visually observed upon at least a portion of the one or more masking colorants of the receiving layer being partially or fully in the final colorless state. The method of the present teachings, may further comprise rendering a colorant layer disposed onto at least a portion of the receiving layer, in which the colorant layer comprises one or more static colorants that are capable of being visually observed upon at least a portion of the one or more masking colorants of the receiving layer being partially or fully in the final colorless state. In some instances, the method of the present teachings may also comprise applying a timing layer disposed onto at least a portion of the activating layer or, in the alternative, disposed onto at least a portion of the receiving layer. The timing layer at least partially retards the rate of migration of the one or more migratory activators into the receiving layer. The method of the present teachings may additionally comprise rendering one or more base substrates, in which at least a portion of at least one of the activating layer or receiving layer is disposed onto the one or more base substrates. In some instances, one of the one or more base substrates may include an indicia area that is capable of being visually observed upon at least a portion of the one or more masking colorants of the receiving layer being partially or fully in the final colorless state.

The present teachings further provide for a method for indicating a predetermined time period has elapsed. The method of the present teachings comprises providing a time validation indicator that comprises a receiving layer and an activating layer. The receiving layer comprises one or more masking colorants and one or more deactivators that cause and maintain the one or more masking colorants to be in an initial colored state. The receiving layer may further comprise one or more polymers that function together with the one or more deactivators to cause and maintain the one or more masking colorants to be in the initial colored state. The activating layer comprises one or more migratory activators that migrate into the receiving layer to cause at least a portion of the one or more masking colorants to advance to a final colorless state that results in a visual color change of the receiving layer. In some aspects, at least one of the activating layer or the receiving layer may further comprise one or more static colorants that are capable of being visually observed upon at least a portion of the one or more masking colorants of the receiving layer being partially or fully in the final colorless state. The time validation indicator may further comprise an adhesive means that bonds together at least a portion of the receiving layer with at least a portion of the activating layer when placed in contact. The time validation indicator may also comprise a colorant layer having one or more static colorants that are capable of being visually observed upon at least a portion of the one or more masking colorants of the receiving layer being partially or fully in the final colorless state. The time validation indicator may optionally comprise a timing layer that at least partially retards the rate of migration of the one or more migratory activators into the receiving layer. The time validation indicator may also comprise one or more base substrates. In some instances, one of the one or more base substrates may include an indicia area that is capable of being visually observed upon at least a portion of the one or more masking colorants of the receiving layer being partially or fully in the final colorless state. The method of the present teachings further comprises placing at least a portion of the receiving layer in contact with at least a portion of the activating layer to initiate the predetermined time period and the migration of the one or more migratory activators into the receiving layer. The method of the present teachings further comprises detecting the visual color change of the receiving layer that indicates the predetermined time period has elapsed. The method of the present teachings may also comprise applying the time validation indicator to at least a portion of a surface of an object.

BRIEF DESCRIPTION OF THE DRAWINGS

The present teachings are illustratively shown and described in reference to the accompany drawings, in which.

DETAILED DESCRIPTION OF THE INVENTION

The present teachings are directed to the creation and use of time validation indicators that can provide a digital and distinct visual indication of expiration of a predetermined time period with the use of at least a receiving layer and an activating layer that, when placed in contact with each other to initiate the predetermined time period, produce a visual color change indicating the predetermined time period has elapsed.

For a better understanding of the disclosure, the following terms are herein defined:

A "liquid carrier medium" is a liquid that acts as a carrier for material(s) distributed in a solid state and/or substantially dissolved therein.

As used herein, a "formulation" is a liquid carrier medium, as defined above, comprising one or more polymers either dissolved in and/or distributed in a solid state within the liquid carrier medium. The formulation may additionally comprise one or more materials that are distributed in a solid state and/or substantially dissolved therein.

A "layer" as used herein refers to a film resulting from the application and substantial drying of a formulation, or in some instances by way of extrusion, injection molding, etc.

The following disclosure describes time validation indicators, as well as the methods and materials for creating such indicators. These indicators possess a number of superior qualities, such as ability to provide digital and distinct indication of a predetermined time period, as well as allow for easy manipulation of the timing period such that these indicators can be utilized for various predetermined time periods, e.g. short, i.e. hour(s), day(s), or week(s), or long, i.e. month(s) or year(s).

Generally speaking, the time validation indicator, according to the present teachings, employs the use of at least a receiving layer that comprises one or more masking colorants and one or more deactivators, and an activating layer that comprises one or more migratory activators that migrate into the receiving layer upon at least a portion of the receiving layer being placed in contact with at least a portion of the activating layer to initiate the predetermined time period. This migration of the one or more migratory activators causes a visual color change of the receiving layer, thereby indicating the predetermined time period has elapsed. It should be noted, that the orientation or ordering of the layers of the time validation indicator is not limited by the schematic drawings which are generally presented herein and for illustrative purposes only. More specifically, the top most layer of the time validation indicator that is viewed by the end user to observe the visual color change may in some instances be that of the activating layer, whereas in other instances may be that of the receiving layer.

Figure 1:
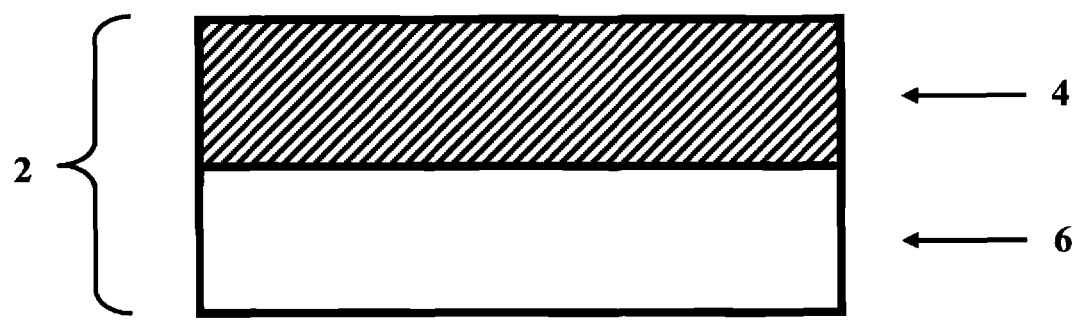
FIG. 1 is a schematic drawing of a time validation indicator according to one aspect of these teachings.

Turning now to FIG. 1, is a schematic illustration of one aspect of the time validation indicator, according to the present teachings. In this example, the time validation indicator (2) comprises a receiving layer (4) and an activating layer (6). The receiving layer (4) comprises one or more masking colorants and one or more deactivators in which the one or more deactivators cause and maintain the one or more masking colorants in an initial colored state, prior to the initiation of the predetermined time period. The activating layer (6) comprises one or more migratory activators which migrate into the receiving layer (4) when at least a portion of the receiving layer (4) is placed in contact with at least a portion of the activating layer (6). Once the receiving layer (4) and activating layer (6) are placed in contact, the predetermined time period and the migration of the one or more migratory activators into that of the receiving layer (4) are initiated, thereby causing at least a portion of the one or more masking colorants to begin to advance to a final colorless state. As the one or more masking colorants advance to the final colorless state over the predetermined time period, a visual color change of the receiving layer (4) occurs. Once at least a portion of the one or more masking colorants reach the final colorless state, the resulting visual color change of the receiving layer (4) indicates that the predetermined time period has elapsed.

Prior to the activation of the time validation indicator, i.e. prior to placing at least a portion of the receiving layer in contact with at least a portion of the activating layer to begin the predetermined time period, the one or more masking colorants in the receiving layer are in an initial colored state by way of the presence of the one or more deactivators. The one or more deactivators, e.g. electron-accepting compounds such as, for example, Lewis acids, clays, or proton-donating compounds, cause and maintain, prior to activation, the one or more masking colorants to be an initial colored state by interacting, chemically or physically, with that of the one or more masking colorants within the receiving layer. In some instances, the receiving layer may further comprise additional one or more polymers that function together with the one or more deactivators to aid in causing and maintaining the one or more masking colorants to be in the initial colored state. In such instances, these additional one or more polymers along with the polymer(s) of the receiving layer may be the same, or in the alternative the one or more polymers may be different than that of the polymer(s) of the receiving layer.

Various colorants may be used as the one or more masking colorants within the receiving layer of the present invention, e.g. dyes. Suitable dyes include, but are not limited to, leuco dyes which are capable of reversibly forming a colored, carbonium ion species such as those depicted in FIGS. 2 and 3. Examples of suitable leuco dyes include, but are not limited to, spiropyrans, benzopyrans, fluoran dyes such as 2'-anilino-3'-methyl-6'-(dibutylamino) fluoran, illustrated in FIG. 2, phthalide dyes such as crystal violet lactone, illustrated in FIG. 3, triarylmethane phthalides, diarylmethane phthalides, or monoheterocyclic substituted phthalides, or those or similar to those described in U.S. patent application Ser. No. 13/178,766, which is incorporated by reference herein in its entirety. It should be noted that the foregoing chromogenic compounds are given for purposes of illustration since any chromogenic compound which is capable of interacting with electron accepting compound(s) may be employed as the one or more masking colorants of the receiving layer. Given that the human eye cannot discriminate optical density changes that occur at high initial density, having, prior to activation of the time validation indicator, the one or more masking colorants in an initial colored state and upon activation, advance to a final colorless state allows for the time validation indicator to provide a more digital color change. This is because the optical density of the receiving layer has to be lowered significantly before the color change of such layer can be perceived. As a result, such an approach, i.e. having the one or more masking colorants advance from an initial colored state to a final colorless state, is contrary to the general approach utilized in prior time indicators.

Figure 2:
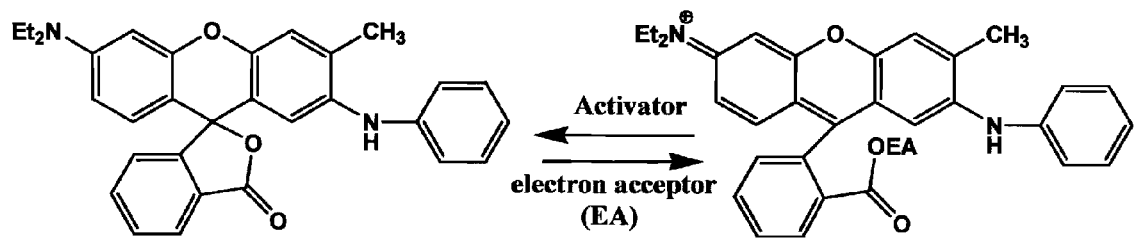
FIG. 2 is an example of a chemical structure and mechanism of coloration of the one or more masking colorants in the instance where the one or more masking colorants are a type of fluoran dye.
Figure 3:
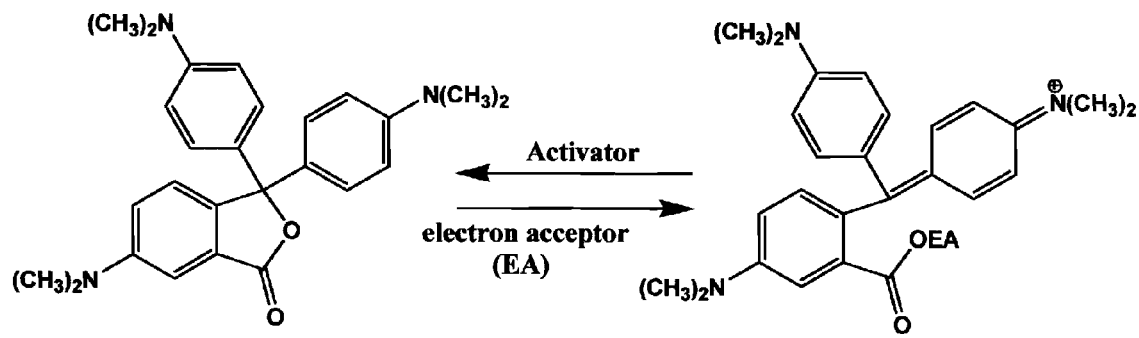
FIG. 3 is an example of a chemical structure and mechanism of coloration of the one or more masking colorants in the instance where the one or more masking colorants are a type of phthalide dye.

In the instances where the one or more masking colorants are one or more leuco dyes, it is generally believed that the color forming reaction of the leuco dye(s) occur through the interaction of the electron donating colorless leuco dye(s) with one or more electron accepting compound(s) to produce the reversible opening of the lactone ring(s), see e.g. FIGS. 2 and 3, yielding the resonance-stabilized cationic leuco dye(s) in the initial colored state. The properties of the color development system, i.e. the one or more leuco dyes and one or more electron-accepting compounds, are a complex subject of investigation and it has become obvious that many parameters can influence the kinetics of the ring opening reaction of the leuco dye(s).

As described in more detail below, a large number of environmental factors can influence whether the one or more leuco dyes, when utilized, are in the opened colored form or the closed colorless form. As a result, this provides great flexibility in adjusting the time validation indicator of the present teachings by way of manipulating the formulation of both the receiving layer and/or the activating layer.

Although not intended to be bound by theory it is believed that in the instance where the one or more masking colorants are that of one or more leuco dyes and the one or more deactivators are one or more electron accepting compounds, the one or more deactivators function as complexing agents or hydrogen bonding agents with the opened form of the leuco dye(s) to generate a conjugated system. The class of leuco dyes that are represented by photochromic dyes such as, the spirooxazines, have been well studied and certain aspects of their characteristics can be related to the leuco fluoran and phthalide lactone type dyes useful in the present invention. Specifically, the environmental conditions that influence the transformation from colorless to colored via opening of the lactone ring appear to be similar for both classes of lactone type dyes. Like the Spirooxazines, the triarylmethane and fluoran leuco dyes are comprised of two aromatic nearly planar moieties. These moieties are linked by a tetrahedral $sp^3$ spiro-carbon which insulates the two $\pi$-electron systems from conjugation. Due to the lack of conjugation, the Spiro type compounds are pale yellow or colorless. However, conditions which favor ring opening and conversion of the spiro compound to a $sp^2$ hybridization result in the aromatic groups aligning its $\pi$-orbitals with each other and forming a conjugated system which is now able to absorb visible light, becoming a highly colored cationic species, see e.g. FIGS. 2 and 3.

Spirooxazines have also been studied in different types of polymers, e.g. cellulose acetate butyrate, polyurethanes, PVC, epoxies, acrylics, polyester, etc., in an attempt to modify their sensitivity to ring opening. These studies show that the ring opening reaction is highly sensitive to the viscosity of their medium. For example, the lowering of the glass transition temperature (Tg) of the host matrix will improve the ease of the transition from colorless to colored and the reverse. The viscosity of the surrounding matrix has a large effect on the opening of the ring system of the one or more leuco dyes because of the size of the fragments that must rotate relative to each other to achieve the $sp^2$ state. This was elegantly demonstrated in "The Generic Enhancement of Photochromic Dye Switching Speeds in a Rigid Polymer Matrix," by R. A. Evans et. al., Nature Materials, Vol. 4 (2005), pp. 249-253, in which covalent photochromic-oligomer conjugates were created and consisting of a leuco dye and a soft, low-Tg oligomer such as, poly(dimethylsiloxane) or poly(ethyleneglycol), to protect the leuco dye from a harsh switching environment, i.e. from a rigid or high-Tg polymer. The leuco dye is protected by the spontaneous coiling of its attached low-viscosity oligomer, which insulates the leuco dye from the surrounding high-Tg, high-viscosity bulk matrix, as described and disclosed in U.S. Pat. No. 7,807,075 which is incorporated by reference herein in its entirety. The leuco dye can be thought of as being permanently lubricated and protected at the molecular level to allow facile ring opening and closing. Furthermore, in "Reversibly Coloring/Decoloring Reaction of Leuco Dye Controlled by Long-Chain Molecule," by Horiguchi et. al, Thin Solid Films, Vol. 516 (2008), pp. 2591-94, has shown that the reversible opening and closing of a similar leuco dye to that of the one or more leuco dyes that may be used in the present invention is regulated by the structural organization of the leuco dye and a long chain electron accepting compound. This structural change shows the occurrence of intercalation and deintercalation of the leuco dye in the reversible coloring process. It is believed that in instances where the one or more masking colorants of the present invention are that of one or more leuco dyes, a similar mechanism is at least partially responsible for the color effect that occurs with the migration of the one or more migratory activators into the receiving layer. It has been shown that the cationic, open form of the leuco dye(s) is not only sensitive to the polarity of solvents, but that protic solvents hydrogen bond to the initial colored state of the leuco dye(s) and thus stabilize it. Therefore with the appropriate choice of the polymer(s) of the receiving layer, i.e. the use of a polymer(s) that will aid in the opening of the one or more leuco dyes through, for example, its hydrogen bonding capacity or polarity, in combination with that of the one or more deactivators, it is possible to cause and maintain the one or more Leuco dyes in an initial colored state, prior to activation of the time validation indicator.

Once the time validation indicator is activated, i.e. placing at least a portion of the receiving layer in contact with at least a portion of the activating layer, the predetermined time is initiated and the one or more migratory activators begin to migrate into the receiving layer causing at least a portion of the one or more masking colorants to advance to a final colorless state, by way of interfering/interacting with at least the complex or hydrogen bonding of the one or more masking colorants in the initial colored state. Suitable migratory activators useful in the present invention include, for example, neutral polyoxygenated compounds such as, polyethylene glycols, polypropylene glycols, polyglycol monoethers or diethers, as well as esters such as, for example, polypropylene glycol 400, polyethylene glycol 400, polyethylene glycol 1000, polyethylene glycol 200, polyethylene glycol 600, polyethylene glycol dimethylether, or polyethylene glycol monolaurate, or nonionic surfactants such as, Triton X 100, or polyethylene oxide-polypropylene oxide block polymers, such as Pluronic®. Other useful compounds such as, amines, e.g. triethanolamine, dioctylamine, tert-octylamine, Tinuvin 292HP, Tinuvin 123, polyethyenimines, Primene JM-T-amine, etc., may be employed as one or more migratory activators in the activating layer.

Figure 4:
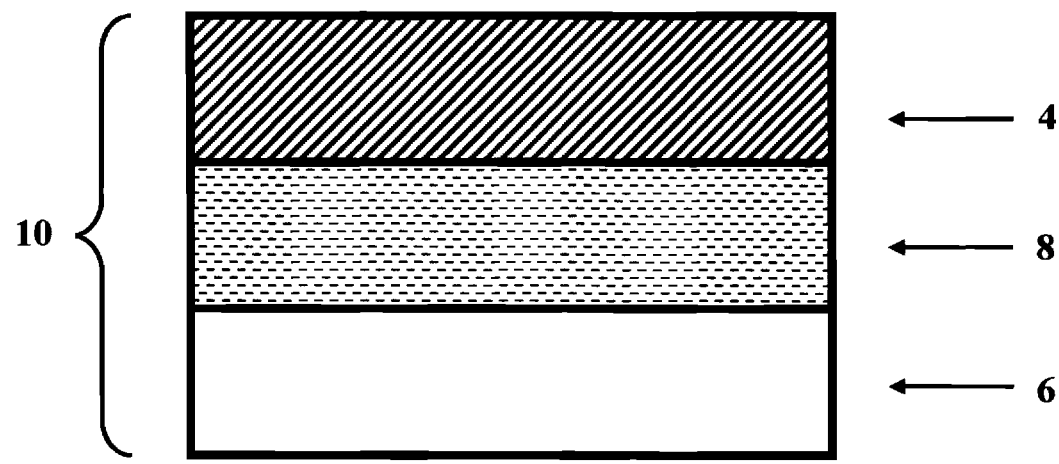
FIG. 4 is a schematic drawing of a time validation indicator according to a second aspect of these teachings.

As stated above, the predetermined time period begins upon the activation of the time validation indicator, i.e. when at least a portion of the receiving layer is placed in contact with at least a portion of the activating layer. In one aspect, according to the present teachings, one or more adhesive materials may be incorporated into at least the receiving layer, activating layer, or both, during formation, to bond together at least a portion of the receiving layer to at least a portion of the activating layer when placed in contact, as well as in some instances, to other additional layers of the time validation indicator. In another aspect, according to the present teachings, as illustrated in FIG. 4, the time validation indicator (10) may further comprise an adhesive layer (8), that comprises one or more adhesive materials, such that the receiving layer (4) and the activating layer (6) are bonded together when at least a portion of the receiving layer (4) is placed in contact with at least a portion of the activating layer (6). In further instances, additional adhesive layers may be utilized to aid in bonding other layers of the time validation indicator with that of the activating layer or receiving layer. The adhesive layer may be either a preformed film of the one or more adhesive materials or in the alternative, prepared by coating the one or more adhesive materials onto a release base, another layer of the time validation indicator, e.g. receiving layer or activating layer, or a base substrate. It should be noted that in instances where the adhesive layer is formed by coating a layer onto a release base, the release base is removed prior to activation of the time validation indicator. The one or more adhesive materials can be any suitable adhesive known in the art, e.g. pressure sensitive adhesives such as, natural or synthetic elastomers, acrylic adhesives, polymers of vinyl ethers or silicone gums, or those or similar to those described in "Pressure-Sensitive Adhesives," by T. M. Goulding, Handbook of Adhesive Technology 2nd Edition, chapter 44 (2003).

Figure 5:
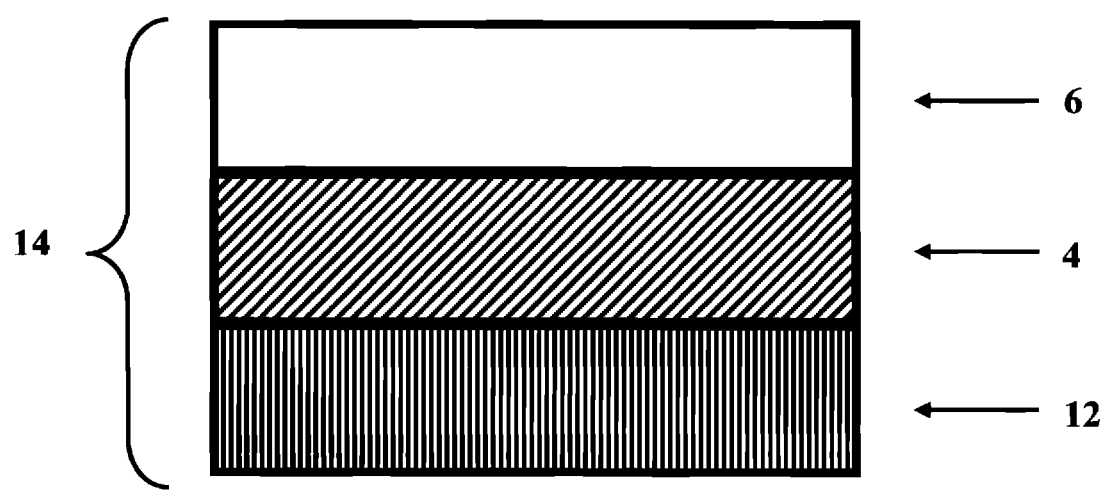
FIG. 5 is a schematic drawing of a time validation indicator according to another aspect of these teachings.

In a further aspect of the present teachings, as illustrated in FIG. 5, the time validation indicator (14) may further comprise a colorant layer (12) disposed onto at least a portion of the receiving layer (4). In other aspects, the colorant layer may be disposed onto at least a portion of the activating layer. In either aspect, the colorant layer comprises one or more static colorants that are capable of being visually observed upon at least a portion of the one or more masking colorants of the receiving layer being partially or fully in the final colorless state. Alternatively, one or more static colorants may be incorporated into the activating layer, the receiving layer, or both. In any of these instances, the one or more static colorants, e.g. dyes, pigments, inks, etc., provide for an increase in the visual contrast between the initial colored state and final colorless state of at least a portion of the one or more masking colorants of the receiving layer, so that a more apparent or distinct visual color change of the receiving layer may result. Thus, the one or more static colorants are generally chosen to display a visual color that substantially contrasts the initial colored state of the one or more masking colorants of the receiving layer. In some instances, it may be desired to incorporate one or more static colorants into the activating layer or receiving layer or both, as well as render another one or more static colorants as a colorant layer disposed onto either the receiving layer or activating layer. In this aspect, a wider color gamut may be produced by the time validation indicator to provide a visual contrasting color to that which is produced by the one or more masking colorants being in the initial colored state, thereby resulting in a greater distinct indication of the visual color change of the receiving layer.

The colorant layer can be prepared by variety methods well known in the art. For example, coating a layer that is generally planar on a release base, another layer of the time validation indicator, e.g. the activating layer or receiving layer, or a base substrate, the layer being prepared from a formulation. Such coatings can be deposited by painting, printing, spraying, slot coating, dip coating, roller coating, bar coating, etc. It should be noted that in instances where the colorant layer is formed by coating a layer onto a release base, the release base is removed prior to activation of the time validation indicator. Alternatively, an effective colorant layer may be prepared by extrusion, injection molding, compression molding, calendaring, thermoforming, etc. In some instances, the colorant layer may also comprise one or more adhesive materials to aid in bonding the colorant layer to other layers of the time validation indicator, e.g. receiving layer or activating layer.

Figure 6:
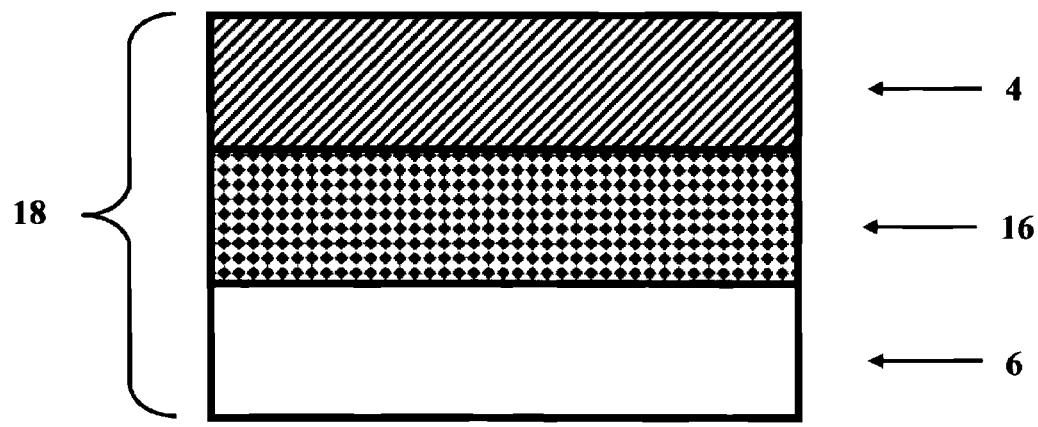
FIG. 6 is a schematic drawing of a time validation indicator according to a further aspect of these teachings.

Referring now to FIG. 6, in a further aspect of the present teachings, the time validation indicator (18) may optionally comprise a timing layer (16), disposed onto at least a portion of either the receiving layer (4) or the activating layer (6), that further regulates or retards the rate of migration of the one or more migratory activators into the receiving layer (4), to lengthen the predetermined time period, if warranted. Suitable materials for the timing layer may include, but are not limited to, polyacrylics, polyurethanes, polycarbonates, polyesters, or fluorinated polymers, and are generally chosen based on the materials ability to slow migration of the one or more migratory activators from the activating layer to the receiving layer. In some instances, the timing layer may also comprise one or more adhesive materials to aid in bonding the timing layer to other layers of the time validation indicator, e.g. receiving layer or activating layer. In other instances, the timing layer may also comprise one or more static colorants that are capable of being visually observed upon at least a portion of the one or more masking colorants of the receiving being partially or fully in the final colorless state. The timing layer can be prepared by coating a layer, by way of e.g. painting, printing, spraying, slot coating, dip coating, roller coating, bar coating, etc., that is generally planar on a release base, another layer of the time validation indicator, e.g. the activating layer or receiving layer, or a base substrate, the layer being prepared from a formulation. It should be noted that in instances where the timing layer is formed by coating a layer onto a release base, the release base is removed prior to activation of the time validation indicator.

Figure 7:
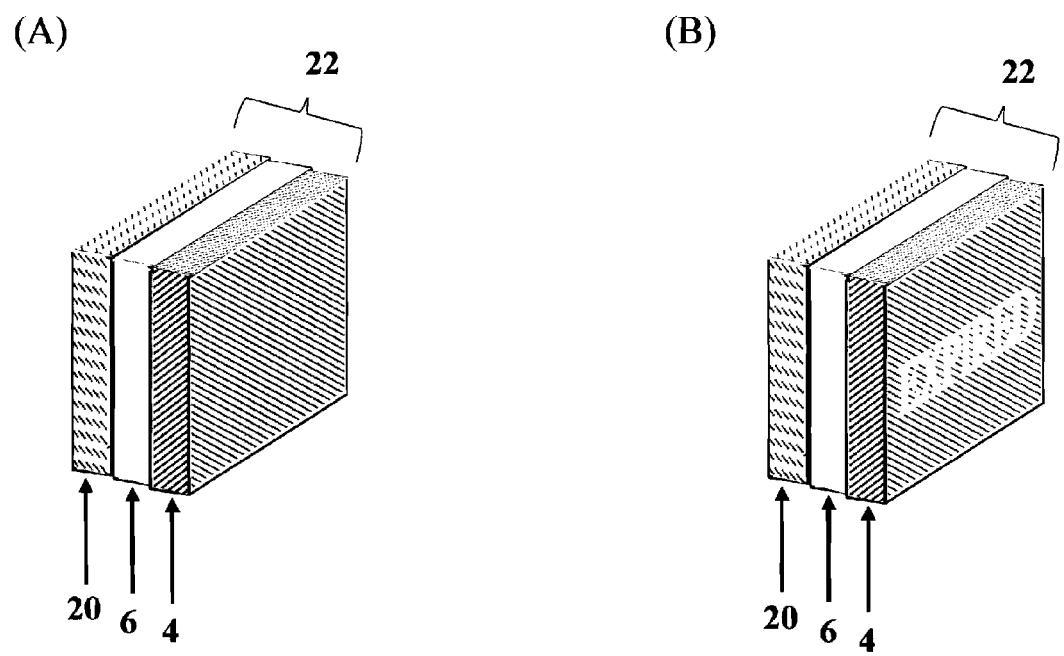
FIG. 7 is a schematic drawing of a time validation indicator according to another aspect of these teachings.

In another aspect of the present teachings, the time validation indicator may further comprise one or more base substrates. In some constructions, at least a portion of the activating layer is disposed onto the one or more base substrates, whereas in other constructions at least a portion of the receiving layer is disposed onto the one or more base substrates. Furthermore in another construction, at least a portion of the activating layer may be disposed onto one of the one or more base substrates and at least a portion of the receiving layer may be disposed onto another one of the one or more base substrates. In some instances, one of the one or more base substrates may include an indicia area indicia area that is capable of being visually observed upon at least a portion of the one or more masking colorants of the receiving layer being partially or fully in the final colorless state. For example, as shown in FIG. 7, the time validation indicator (22) includes one of the one or more base substrates (20) having an indicia area in the form of the word EXPIRED. FIG. 7A illustrates the time validation indicator (22) prior to at least a portion of the one or more masking colorants being partially or fully in the final colorless state, in which the indicia area is visually undetectable, whereas FIG. 7B illustrates the visual appearance of the indicia area of the time validation indicator (22) upon at least a portion the one or more masking colorants being partially or fully in the final colorless state. Suitable base substrates to be used in the present invention may include any material suited for printing or coating, e.g. Mylar film. In some instances, the surface of an object may serve as the base substrate. In alternative instances, an indicia area may be applied onto any of the layers of the time validation indicator. The indicia area may be printed or coated onto a base substrate or a layer in the form of a message or other numeric or alphabetic symbols, or shapes, etc., so that the indicia area may become visually apparent following the visual color change of the receiving layer. In a further aspect, the indicia area may be rendered into the activating layer or receiving layer by way of incorporating one or more static colorants in the form of a message or other numeric or alphabetic symbols, or shapes, etc., so that the indicia area may become visually apparent following the visual color change of the receiving layer. The indicia area may be any color or more specifically, a color that enhances the contrast between the initial colored state and final colorless state of the one or more masking colorants of the receiving layer.

In other aspects, the indicia area may in the form of a bar code which becomes altered following the migration of the one or more migratory activators into the receiving layer during the predetermined time period. In such instance, upon the alteration of the bar code, a conventional bar code reading device can be used to read the altered bar code and indicate that the predetermined time period has elapsed.

According to the present teachings, the layers of the time validation indicator include one or more polymers that act as a binder. Examples of polymers that are useful in each layer of the present invention include, but are not limited to, acrylic polymers such as, Elvacite® (Lucite) 2014 or NeoCryl® B818 (DSM), polyurethanes such as, MACE 107-295, or fluorinated polymers, such as FC 2230. It should be noted that the type of polymer(s) used for each layer of the time validation indicator may in some instances be the same, whereas in others, different. The choice of polymer(s) for each layer will depend on solubility factors associated with the various materials in each layer. Any type of polymer(s) which allow the constituents of the activating layer to migrate into the receiving layer is acceptable for use. Furthermore, in terms of the receiving layer, the one or more polymers chosen to be included within such layer also aid the one or more deactivators in causing and maintaining the one or more masking colorants in the initial colored state. This is because in some instances, the one or more deactivators alone may not effectively cause and maintain the one or more masking colorants in the initial colored state.

To further aid in the regulation of the predetermined time period, any of the foregoing layers of the time validation indicator may further comprise one or more plasticizers. Plasticizers, most commonly phthalate esters, are additives used in polymers to impart improved flexibility and durability. Plasticizers work by embedding themselves between the chains of polymer(s) thereby increasing the "free volume", and thus substantially lowering the glass transition temperature (Tg) of the polymer(s) and making it softer. In other words, as a plasticizer migrates into the polymer(s) it disrupts the intermolecular forces between polymer chains and thus allows for better movement between polymer segments lowering the Tg which allows for easy migration of other constituents, for example the one or more migratory activators into that of the receiving layer.

Additional components that may be incorporated within any of the foregoing layers of the time validation indicator include, but are not limited to, dispersant(s), thickener(s), wetting agent(s), defoamer(s), etc., that do not cause the one or more masking colorants of the receiving layer to advance to a final colorless state before the predetermined time period begins. Dispersants, wetting agents, or defoamers may each be oligomeric, polymeric, or copolymeric materials or blends containing surface-active (surfactant) characteristic blocks, such as, for example, polyethers, polyols, or polyacids. Examples of dispersants include acrylic acid-acrylamide polymers, or salts of amine functional compound and acid, hydroxyfunctional carboxylic acid esters with pigment affinity groups, and combinations thereof, for example DISPERBYK®-180, DISPERBYK®-181, DISPERBYK®-108, all from BYK-Chemie, and TECO® Dispers 710 from Degussa GmbH. Wetting agents are suitable surfactant materials, and may be selected from among polyether siloxane copolymers, for example, TEGO® Wet 270, non-ionic organic surfactants, for example, TEGO®

Wet 500, and combinations thereof. Defoamers may be organic modified polysiloxanes, for example, TEGO® Airex 900.

The timing period between placing the layers of the time validation indicator in contact with one another and the visual color change of the receiving layer depends on a series of variables that are controllable and allow for the manipulation of the time validation indicator, in accordance with the present teachings, for various predetermined time periods. Since the visual color change of the receiving layer depends on the migration kinetics of the one or more migratory activators, any parameter that affects such kinetics will, as a result, also affect the timing period and therefore, may be utilized in varying the timing period of the present invention to match the predetermined time period desired. Examples of such parameters include, but are not limited to, the concentration of the one or more deactivators, the concentration of the one or more migratory activators, and/or the types of the one or more migratory activators, all described in more detail below. It should be noted that the graphs of FIGS. 8-12 were based on a mathematical model derived from the optical density changes over time, i.e. the relation between density and time of contact (activation), of various examples of the time validation indicator of the present teachings. The optical density changes were measured using a MacBeth Spectrolino. This relationship provided a mathematical regression which was then used for normalization and extrapolation to create the graphs illustrated in FIGS. 8-12.

Figure 8:
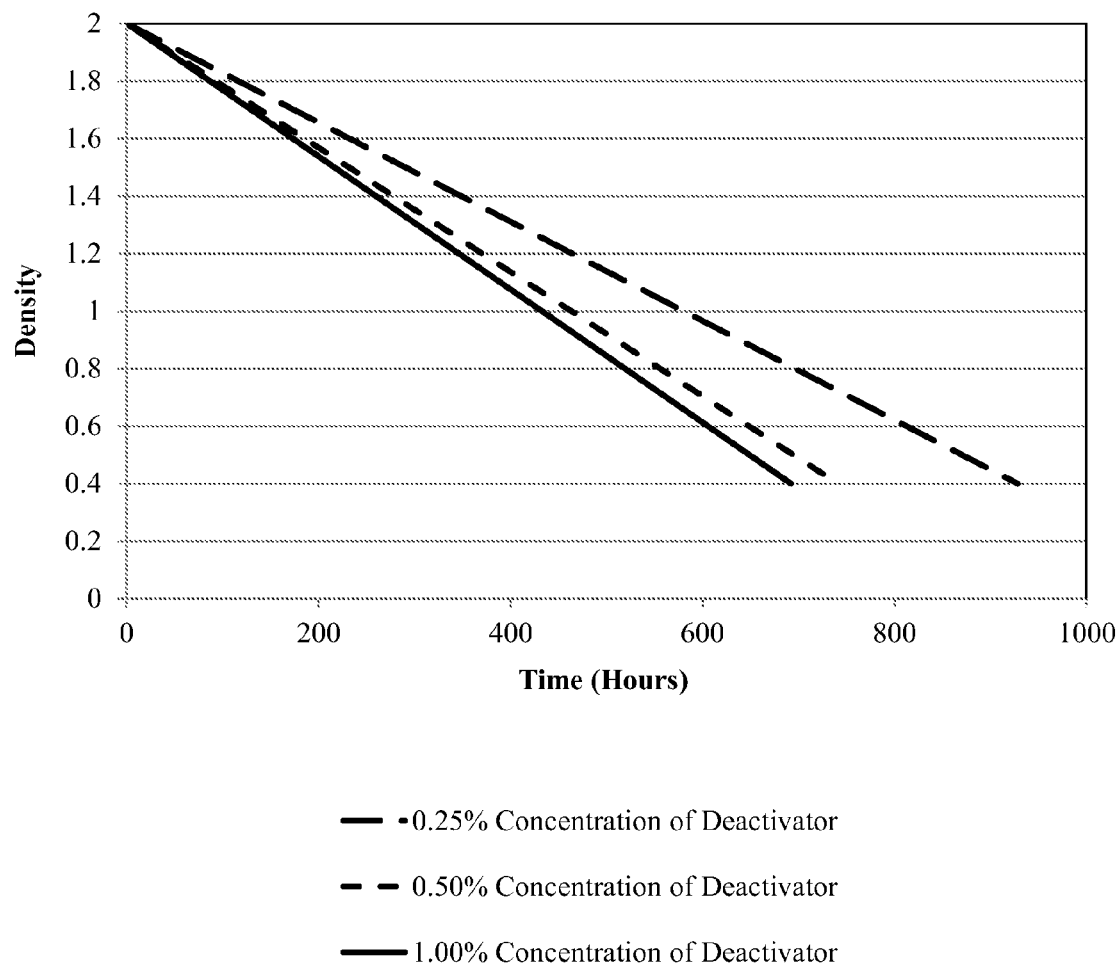
FIG. 8 is a graph illustrating the affect different concentrations of one or more deactivators have on the timing period of the present invention.

By way of example, FIG. 8 depicts the affect varying concentrations of the one or more deactivators in the receiving layer have on the timing period of the present invention. In this example, three different receiving layers were provided that included malonic acid as the deactivator. The first receiving layer comprised a malonic acid concentration of 0.25%, the second receiving layer comprised a malonic acid concentration of 0.50%, and the third receiving layer comprised layer a malonic acid concentration 1.00%. In addition, each of the three different receiving layers also included 0.5% Black Dye 400 as the masking colorant and 20% FC-2230 fluoroelastomer. Three common activating layers were provided each comprising 20% polyethylene glycol dimethylether (PEGDME) as the migratory activator with 20% plasticizer, P-670, in 28% Elvacite® 2014. Each receiving layer was placed in contact with a respective activating layer and then monitored for changes in optical density over time using a MacBeth Spectrolino. As shown in FIG. 8, it was determined that by increasing the concentration of the one or more deactivators, from 0.25% to 1.00%, it took approximately 240 hours longer for the time validation indicator of the present teachings to reach the same optical density with 1.00% concentration of the deactivator versus 0.25% concentration of the deactivator. Furthermore, the type of one or more deactivators, e.g. maleic acid, malic acid, fumaric acid, terephthalic acid, propyl gallate, etc., can also further affect the migration kinetics of the one or more migratory activators into that of the receiving layer of the time validation indicator of the present teachings.

Figure 9:
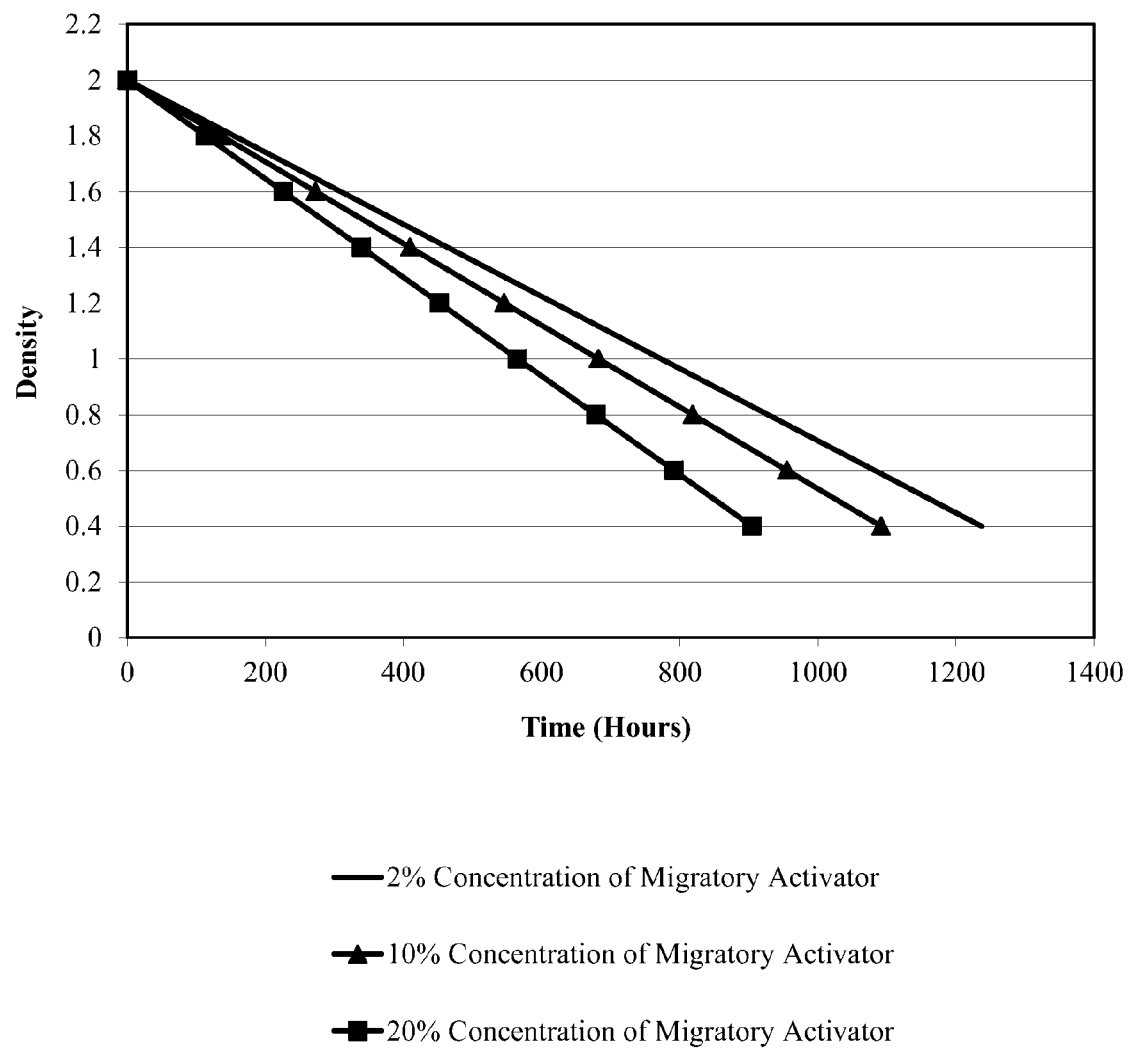
FIG. 9 is a graph illustrating the affect different concentrations of one or more migratory activators have on the timing period of the present invention.
Figure 10:
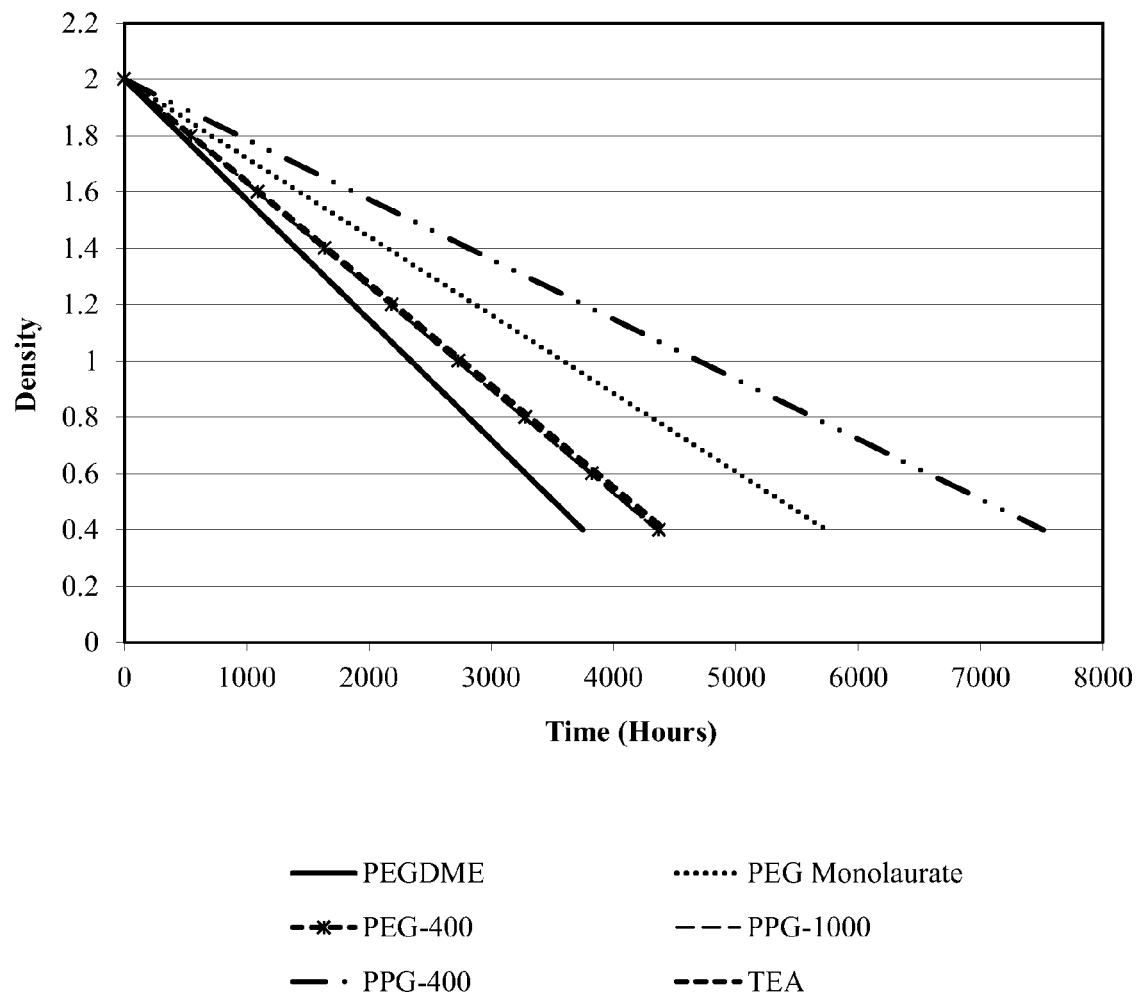
FIG. 10 is a graph illustrating the affect various types of one or more migratory activators have on the timing period of the present invention.

In another example, now referring to FIG. 9, the concentration of the one or more migratory activators may also influence the timing period of the present invention. In this example, three different activating layers were provided that included PEDGME as the migratory activator. The first activating layer comprised a PEDGME concentration of 2%, the second activating layer comprised a PEDGME concentration of 10%, and the third activating layer comprised a PEDGME concentration of 20%. In addition, each of the three different activating layers also included 10% P-670 in 28% Elvacite® 2014. Three common receiving layers were also provided each comprising 0.5% Black Dye 400 as the masking colorant and 1% malonic acid as the deactivator in 20% FC-2230 fluoroelastomer. Each activating layer was placed in contact with its respective receiving layer and then monitored for changes in optical density over time using a MacBeth Spectrolino. As seen in FIG. 9, increases in PEGDME concentration, i.e. from 2% to 10% to 20%, led to a decreased timing period, as expected, since higher concentration levels of the one or more migratory activators will increase the rate the one or more masking colorants advance from the initial colored state to the final colorless state. In addition to varying the concentration of the one or more migratory activators, the types of the one or more migratory activators utilized in the activating layer also affects the timing period of the present invention, as illustrated in FIG. 10. Now referring to FIG. 10, six common receiving layers were provided each one having the same composition as the receiving layers in FIG. 9 and six different activating layers were provided each having a different type of migratory activator at 2% concentration with 10% P-670 in 28% Elvacite® 2014. Each activating layer was placed in contact with its respective receiving layer and then monitored for changes in optical density over time using a MacBeth Spectrolino. As depicted in FIG. 10 the type of migratory activator(s) used within the activating layer may substantially alter the timing period of the time validation indicator of the present teachings.

In addition to the above mentioned parameters, the glass transition temperature (Tg) and/or the polarity of the polymer(s) of the activating layer and/or the receiving layer, and/or the thickness of the layers included in the time validation indicator can also affect the timing period. In instances where the time validation indicator also includes an adhesive layer disposed between the receiving layer and activating layer, the composition of the adhesive layer may also affect the migration kinetics of the one or more migratory activators, thereby affecting the timing period. In other instances where the time validation indicator also comprises a timing layer disposed between the receiving layer and the activation layer, the polymer(s), as well as the thickness of such timing layer, may also affect the migration kinetics of the one or more migratory activators. Furthermore, it has also been found that the concentration of the one or more masking colorants may also influence the migration kinetics of the one or more migratory activators. For example, in the instance where black leuco dye(s) are the one or more masking colorants, it was found that not only the thickness of the receiving layer, but the concentration of the black leuco dye(s) can affect the amount of time it takes for such dye(s) to go from an initial colored state to that of a final colorless state. Therefore, the higher the concentration of the one or more masking colorants present in the receiving layer, the longer the timing period, which is also similar to the affect the concentration of the one or more deactivators may have on the timing period.

Figure 11:
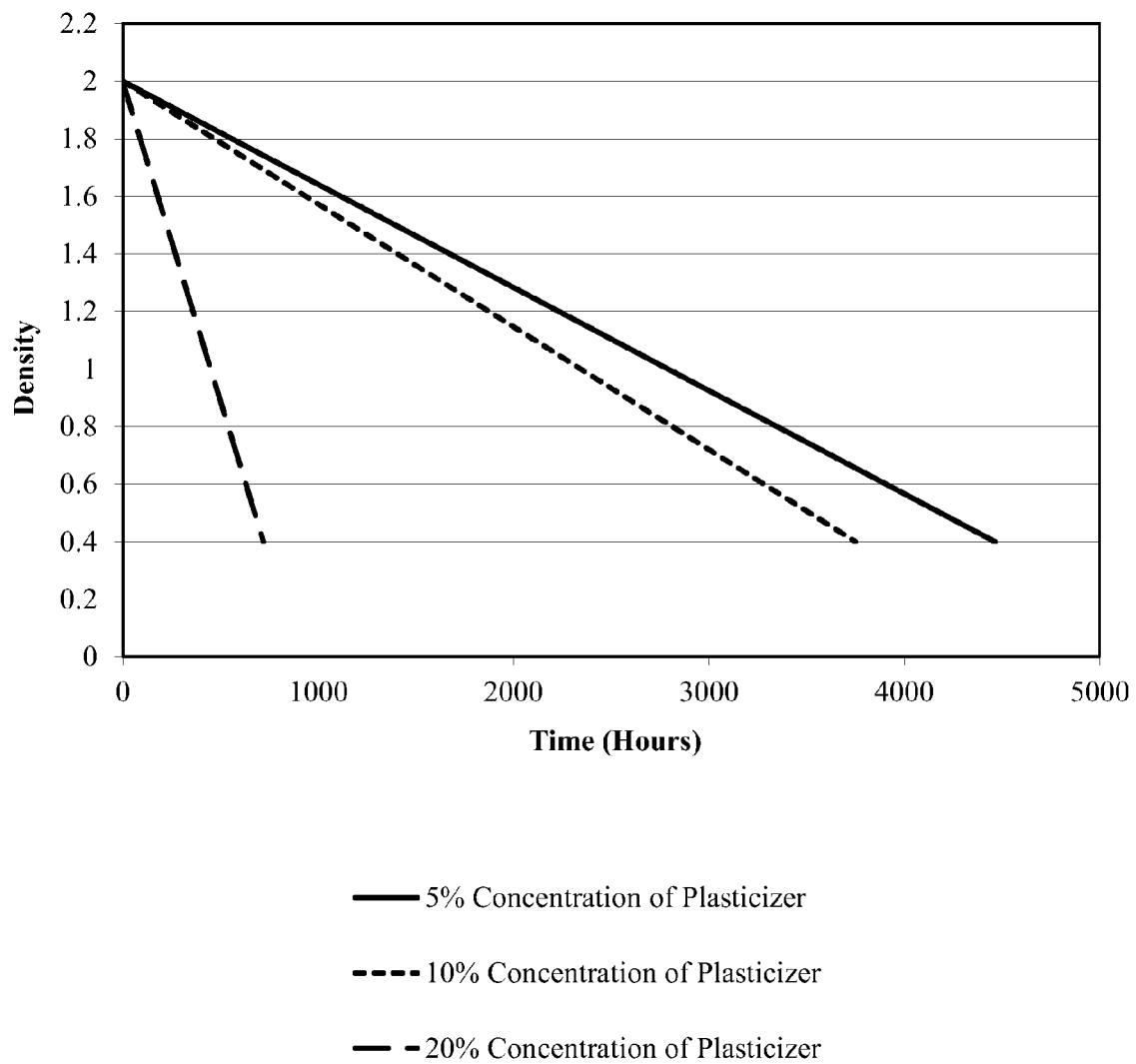
FIG. 11 is a graph illustrating the affect different concentrations of one or more plasticizers within the activating layer have on the timing period of the present invention.
Figure 12:
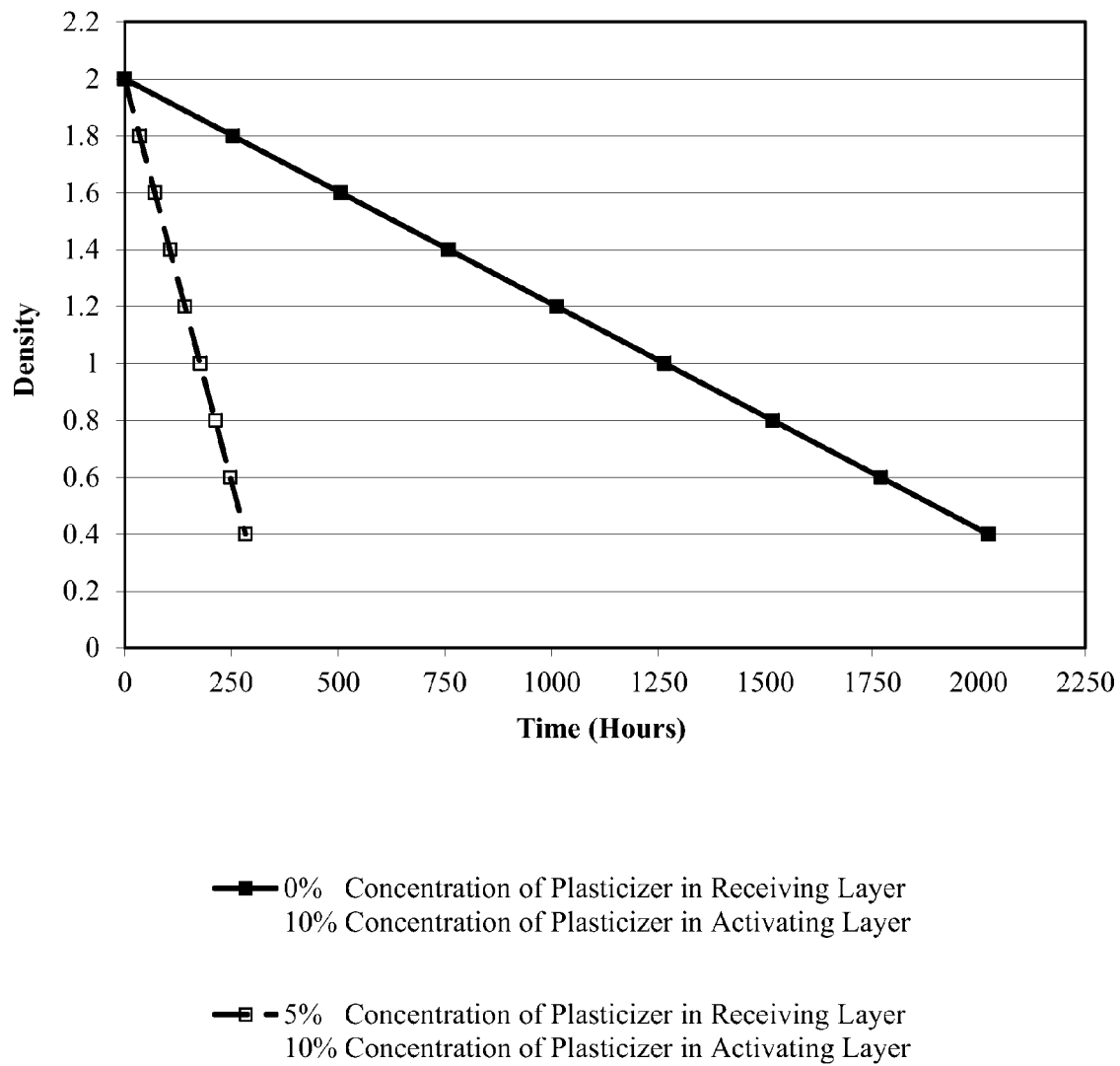
FIG. 12 is a graph illustrating the affect different concentrations of one or more plasticizers within the receiving layer and activating layer have on the timing period of the present invention.

In any aspect of the time validation indicator of the present teachings, the final migration kinetics of the one or more migratory activators can be managed by the use of one or more plasticizers incorporated into at least the activating layer as shown by way of example in FIG. 11. In this example three different activating layers were provided each having 2% PEGDME in 28% Elvacite® 2014, as well as plasticizer, P-670. The plasticizer concentration of the first activating layer was 5%, the plasticizer concentration of the second activating layer was 10%, and the plasticizer concentration in the third activating layer was 20%. Three common receiving layers were also provided, each comprising 0.5% Black Dye 400 with 1% malonic acid in 20% FC-2230 fluoroelastomer. Each activating layer was placed in contact with its respective receiving layer and then monitored for changes in optical density over time using a MacBeth Spectrolino. As shown in FIG. 11, a change in timing period results due to the concentration level of the P-670 present in the activating layer, i.e. the higher concentrations of P-670 can lead to faster migration kinetics and shorter timing periods of the present invention, since the one or more plasticizers not only lowers the Tg of the FC-2230 polymer within the receiving layer, but also allows for ease of migration of the migratory activator PEGDME. In addition to the activating layer, in some instances, the receiving layer may also comprise one or more plasticizers, as illustrated by way of example in FIG. 12. Now referring to FIG. 12, two different receiving layers were provided, each comprising 0.5% Black Dye 400 with 1% malonic acid in 20% FC-2230 fluoroelastomer. One of the receiving layers also comprised a plasticizer, P-670, at 5% concentration. In addition, two common activating layers were also provided, each having 2% PEGDME with 10% plasticizer, P-670, in 28% Elvacite® 2014. Each receiving layer was placed in contact with its respective activating layer and then monitored for changes in optical density over time using a MacBeth Spectrolino. As seen in FIG. 12, in the instances where both the activating layer and receiving layer comprise one or more plasticizers, the timing period of the present invention can be substantially shortened due to the one or more plasticizers of the receiving layer aiding in the migration kinetics of the one or more migratory activators. Thus, various combinations of plasticizer concentrations in the activating layer and/or the receiving layer can be used to further adapt the timing period, such that the time validation indicator of the present teachings can be used to determine the expiration of a wide variety of time intervals. Optionally, one or more plasticizers may also be incorporated into any additional layers that may be included within the time validation indicator of the present teachings to further aid in the migration kinetics of the one or more migratory activators.

The time validation indicator, according to the present teachings, may be fabricated by any method well known to those skilled in the art. One such method may include forming a receiving layer, forming an activating layer, and placing at least a portion of the receiving layer in contact with at least a portion of the activating layer to initiate the predetermined time period and the migration of the one or more migratory activators into the receiving layer. A variety of methods can be used to form an effective receiving layer and activating layer. Such methods may include coating a layer, by way of e.g. painting, printing, spraying, slot coating, dip coating, roller coating, bar coating, etc., that is generally planar on a release base, a surface of an object, another layer of the time validation indicator, or a base substrate, the layer being prepared from a formulation. It should be noted that in instances where the receiving layer or activating layer is formed by coating a layer onto a release base, the release base is removed prior to activation of the time validation indicator. Alternatively, an effective receiving layer or activating layer may be prepared by extrusion, injection molding, compression molding, calendaring, thermoforming, etc. The placing of at least a portion of the receiving layer in contact with at least a portion of the activating layer may include either direct contact, i.e. no additional layers are disposed between the activating layer and receiving layer, or indirect contact, i.e. one or more additional layers are disposed between the activating layer and the receiving layer, e.g. an adhesive layer and/or a timing layer. In some instances, the placing of at least a portion of the receiving layer in contact with at least a portion of the activating may be done without the use of an adhesive means, while in other instances adhesive means may be utilized. The adhesive means, if used, bonds together at least a portion of the receiving layer to at least a portion of the activating layer when placed in contact. The adhesive means may be applied by rendering an adhesive layer onto at least a portion of the receiving layer and/or the activating layer, or in the alternative by incorporating one or more adhesive materials into the receiving layer and/or the activating layer during formation. In another aspect, the method may further include rendering a colorant layer disposed onto at least a portion of either the receiving layer or the activating layer. In other instances, the method may also include applying a timing layer disposed onto at least a portion of the receiving layer or the activating layer. In further aspects, the method may optionally include rendering one or more base substrates, in which at least a portion of at least the activating layer or the receiving layer is disposed onto the one or more base substrates. It should be noted that additional adhesive means may also be utilized to bond other layers, e.g. colorant layer and/or timing layer, if present, to that of the activating layer, receiving layer, or a base substrate.

The time validation indicators, according to the present teachings, are applicable to various instances that warrant an indication of the elapse of a predetermined time period. For example, the expiration of a shelf-life of an object, general inventory management, etc. One method for indicating a predetermined time period has elapsed may include providing a time validation indicator, in accordance with the present teachings, placing at least a portion of the receiving layer in contact with at least a portion of the activating layer to initiate the predetermined time period and the migration of the one or more migratory activators into the receiving layer, and detecting the visual color change of the receiving layer that indicates the predetermined time period has elapsed. In a further aspect, the method may also include applying the time validation indicator to at least a portion of an object. The adaptability of the layers of the time validation indicator according to the present teachings, enables the time validation indicator to be utilized for a host of different time intervals and therefore instances in which visual indication of the elapse of a predetermined time period is sought.

EXEMPLIFICATIONS

The present teachings, having been generally described, will be more readily understood by reference to the following examples, which are included merely for the purposes of illustration of certain aspects and embodiments of the present teachings, and are not intended to limit the scope of these teachings. It should be noted that, unless otherwise specified, the weight % values mentioned in the below examples are measured relative to a solid state.

Example 1

Preparation of a Time Validation Indicator with a Predetermined Time Period of Approximately 144 Hours Receiving Layer:
To 25.0 g of a magnetically stirred solution of 20% FC-2230 fluoroelastomer (3M, Dyneon) in ethyl acetate is added 0.5% (0.025 g) Black Dye 400 from Yamada Chemical Co., 1% (0.050 g) Malonic Acid from Aldrich Chemical and 5% Plasthall P-670 from Hallstar (1.39 g based on total weight of components including the Plasthall). This formulation was stirred at room temperature for 30 minutes until fully dissolved and then sonicated (Branson 2200) for 15 minutes at room temperature to remove air bubbles and to insure a uniform mixture. This formulation was then coated on a base substrate, Mylar film of 10 mils, using a 20 mil Bird bar and dried at 40° C. for 4 hours and then at 80° C. for 14 hours to yield a receiving layer.

Activating Layer:
To 25.0 g of a magnetically stirred solution of 28% Elvacite® 2014 (Lucite International/Chempoint) in toluene is added 20% (0.35 g) polyethylene glycol dimethylether (Aldrich), and 20% Plasthall-P670 (6.63 g based on total weight of components including the Plasthall). This formulation was stirred at room temperature for 30 minutes until fully dissolved and then sonicated (Branson 2200) for 15 minutes at room temperature to remove air bubbles and to insure a uniform mixture. This formulation was then coated on a base substrate, Mylar film of 10 mils, using a 20 mil Bird bar and dried at 40° C. for 4 hours and then at 80° C. for 14 hours to yield an activating layer.

Adhesive Layer:
Prepared by coating #9026 transfer adhesive (3M) onto the activating layer to yield an adhesive layer.

The receiving layer was then cold laminated to the adhesive layer, thereby placing at least a portion of the receiving layer in contact with at least a portion of the activating layer to begin the predetermined time period and initiate the migration of the one or more migratory activators into the receiving layer causing at least a portion of the one or more masking colorants to advance to a final colorless state.

Example 2

Preparation of a Time Validation Indicator with a Predetermined Time Period of Approximately 4300 Hours Receiving Layer:
Prepared as in Example 1.

Timing Layer:
To 25.0 g of a magnetically stirred solution of 28% Elvacite® 2014 is added 5% Plasthall-P670 (1.39 g based on total weight of components including the Plasthall). This formulation was stirred at room temperature for 30 minutes until fully dissolved and then sonicated (Branson 2200) for 15 minutes at room temperature to remove air bubbles and to insure a uniform mixture. This formulation was then coated on a release base using a 20 mil Bird bar and dried in an oven at 40° C. for 4 hours and then at 80° C. for 14 hours to yield a timing layer. The timing layer was then heat laminated to the receiving layer.

Activation Layer:
To 25.0 g of a magnetically stirred solution of 28% Elvacite® 2014 in toluene is added 20% (0.35 g) polyethylene glycol dimethylether, and 10% Plasthall-P670 (2.95 g based on total weight of components including the Plasthall). This formulation was stirred at room temperature for 30 minutes until fully dissolved and then sonicated (Branson 2200) for 15 minutes at room temperature to remove air bubbles and to insure a uniform mixture. This formulation was then coated on a base substrate, Mylar film of 10 mils, using a 20 mil Bird bar and dried at 40° C. for 4 hours and then at 80° C. for 14 hours to yield an activating layer.

Adhesive Layer:
Prepared by coating #9026 transfer adhesive (3M) onto the activating layer to yield an adhesive layer.

The timing layer was then cold laminated to the adhesive layer, thereby placing at least a portion of the receiving layer in contact with at least a portion of the activating layer to begin the predetermined time period and initiate the migration of the one or more migratory activators into the receiving layer causing at least a portion of the one or more masking colorants to advance to a final colorless state.

Example 3

Preparation of a Time Validation Indicator with a Predetermined Time Period of Approximately 330 Hours Receiving Layer:
To 25.0 g of a magnetically stirred solution of 20% FC-2230 fluoroelastomer in ethyl acetate is added 1.0% (0.050 g) Black Dye 400, and 1% (0.050 g) malonic acid. This formulation was stirred at room temperature for 30 minutes until fully dissolved and then sonicated (Branson 2200) for 15 minutes at room temperature to remove air bubbles and to insure a uniform mixture. This formulation was then coated onto a base substrate, Mylar film of 2 mils, using a 20 mil Bird bar and dried at 40° C. for 4 hours and then at 80° C. for 14 hours to yield a receiving layer.

Timing Layer:
To 25.0 g of a magnetically stirred solution of 28% Elvacite® 2014 is added 5% Plasthall-P670 (1.39 g based on total weight of components including the Plasthall). This formulation was stirred at room temperature for 30 minutes until fully dissolved and then sonicated (Branson 2200) for 15 minutes at room temperature to remove air bubbles and to insure a uniform mixture. This formulation was then coated on a release base using a 20 mil Bird bar and dried in an oven at 40° C. for 4 hours and then at 80° C. for 14 hours to yield a timing layer.

Colorant Layer:
To 25.0 g of a magnetically stirred solution of 28% Elvacite® 2014 in toluene is added 10% (0.70 g) of Red BSR-RD213 (Brilliant). This formulation was stirred at room temperature for 30 minutes until fully dissolved and then sonicated (Branson 2200) for 15 minutes at room temperature to remove air bubbles and to insure a uniform mixture. This formulation was then coated onto a base substrate, Mylar film of 2 mils, using a 20 mil Bird bar and dried at 40° C. for 4 hours and then at 80° C. for 14 hours to yield a colorant layer.

Adhesive Layer 1:

Prepared by coating #9026 transfer adhesive (3M) onto the colorant layer to yield an adhesive layer.

Activating Layer:

To 25.0 g of a magnetically stirred solution of 28% Elvacite® 2014 in toluene is added 10% (0.175 g) polyethylene glycol dimethylether, and 20% Plasthall-P670 (6.30 g based on total weight of components including the Plasthall). This formulation was stirred at room temperature for 30 minutes until fully dissolved and then sonicated (Branson 2200) for 15 minutes at room temperature to remove air bubbles and to insure a uniform mixture. This formulation was then coated on a release base, Mylar film of 2 mils, using a 20 mil Bird bar and dried at 40° C. for 4 hours and then at 80° C. for 14 hours to yield an activating layer.

Adhesive Layer 2:

Prepared by coating #9026 transfer adhesive (3M) onto the activating layer to yield an adhesive layer.

The adhesive layer 1 was cold laminated to one side of the receiving layer and the timing layer was cold laminated to the opposing side of the receiving layer. The adhesive layer 2 was then cold laminated to the timing layer, thereby placing at least a portion of the receiving layer in contact with at least a portion of the activating layer to begin the predetermined time period and initiate the migration of the one or more migratory activators into the receiving layer causing at least a portion of the one or more masking colorants to advance to a final colorless state.

For the purposes of describing and defining the present teachings, it is noted that the term "substantially" is utilized herein to represent the inherent degree of uncertainty that may be attributed to any quantitative comparison, value, measurement or other representation. The term "substantially" is also utilized herein to present the degree by which a quantitative representation may vary from a stated reference without resulting in a change in the basic function of the subject matter at issue.

Although the teachings have been described with respect to various embodiments, it should be realized that these teachings are also capable of a wide variety of further and other embodiments within the spirit and scope of the appended disclosure.

What is claimed is:

1. A time validation indicator, said time validation indicator comprising:
    a receiving layer that comprises:
        (i) one or more masking colorants; and
        (ii) one or more deactivators that cause and maintain said one or more masking colorants in an initial colored state, wherein the one or more deactivators are one or more electron accepting compounds; and
    an activating layer that comprises one or more migratory activators that migrate into said receiving layer upon at least a portion of said receiving layer being placed in contact with at least a portion of said activating layer to initiate a predetermined time period, wherein the migration of said one or more migratory activators into said receiving layer causes at least a portion of said one or more masking colorants to advance to a final colorless state resulting in a visual color change of said receiving layer that indicates the predetermined time period has elapsed.

2. The time validation indicator of claim 1, wherein said one or more masking colorants are one or more leuco dyes.

3. The time validation indicator of claim 2, wherein the leuco dye is a spiropyran, benzopyran, fluoran dye, phthalide dye, triarylmethane phthalide, diarylmethane phthalide, or monoheterocyclic substituted phthalide.

4. The time validation indicator of claim 3, wherein said fluoran dye is 2'-anilino-3'-methyl-6'-(dibutylamino) fluoran.

5. The time validation indicator of claim 3, wherein said phthalide dye is crystal violet lactone.

6. The time validation indicator of claim 1, wherein said one or more migratory activators are one or more polyoxygenated compounds.

7. The time validation indicator of claim 6, wherein the one or more polyoxygenated compounds are neutral polyoxygenated compounds.

8. The time validation indicator of claim 7, wherein the neutral polyoxygenated compound is polyethylene glycol, polypropylene glycol, polyglycol monoether, polylpolyglycol diether, polypropylene glycol 400, polyethylene glycol 400, polyethylene glycol 1000, polyethylene glycol 200, polyethylene glycol 600, polyethylene glycol dimethyl ether, polyethylene glycol monolaurate, a nonionic surfactant, polyethylene oxide-polypropylene oxide block polymer, triethanolamine, dioctylamine, tertoctylamine, or polyethyleneimine.

9. The time validation indicator of claim 1, wherein at least one of said receiving layer or said activating layer further comprises one or more plasticizers that aid in the migration of said one or more migratory activators into said receiving layer.

10. The time validation indicator of claim 1, wherein at least one of said receiving layer or said activating layer further comprises at least one of one or more dispersants, one or more thickeners, one or more wetting agents, or one or more defoamers.

11. The time validation indicator of claim 1, wherein said receiving layer further comprises one or more polymers that function together with said one or more deactivators to cause and maintain said one or more masking colorants to be in said initial colored state.

12. The time validation indicator of claim 11, wherein the one or more polymers are fluoroelastomers.

13. The time validation indicator of claim 1, wherein at least one of said receiving layer or said activating layer further comprises one or more adhesive materials that bond together at least a portion of said receiving layer to at least a portion of said activating layer when placed in contact.

14. The time validation indicator of claim 1, furthering comprising an adhesive layer that bonds together at least a portion of said receiving layer to at least a portion of said activating layer when placed in contact.

15. The time validation indicator of claim 1, wherein at least one of said activating layer or said receiving layer further comprises one or more static colorants that are capable of being visually observed upon at least a portion of said one or more masking colorants of said receiving layer being partially or fully in said final colorless state.

16. The time validation indicator of claim 1, further comprising a colorant layer that comprises one or more static colorants that are capable of being visually observed upon at least a portion of said one or more masking colorants of said receiving layer being partially or fully in said final colorless state.

17. The time validation indicator of claim 1, further comprising a timing layer that at least partially retards the rate of migration of said one or more migratory activators into said receiving layer.

18. The time validation indicator of claim 1, further comprising one or more base substrates.

19. The time validation indicator of claim 18, wherein one of said one or more base substrates comprises an indicia area that is capable of being visually observed upon at least a portion of said one or more masking colorants of said receiving layer being partially or fully in said final colorless state.

20. The time validation indicator of claim 1, wherein the electron accepting compound is a Lewis acid, a clay, or a proton-donating compound.

21. The time validation indicator of claim 1, wherein the electron accepting compound is malonic acid, maleic acid, malic acid, fumaric acid, terephthalic acid, or propyl gallate.

22. A method for fabricating a time validation indicator, said method comprising:
   forming a receiving layer that comprises:
      (i) one or more masking colorants; and
      (ii) one or more deactivators that cause and maintain said one or more masking colorants in an initial colored state, wherein the one or more deactivators are one or more electron accepting compounds;
   forming an activating layer that comprises one or more migratory activators that migrate into said receiving layer upon at least a portion of said receiving layer being placed in contact with at least a portion of said activating layer to initiate a predetermined time period; and
   placing at least a portion of said receiving layer in contact with at least a portion of said activating layer to initiate the predetermined time period and the migration of said one or more migratory activators into said receiving layer,
   wherein the migration of said one or more migratory activators into said receiving layer causes at least a portion of said one or more masking colorants to advance to a final colorless state resulting in a visual color change of said receiving layer that indicates the predetermined time period has elapsed.

23. The method of claim 22, further comprising applying an adhesive means that bonds together at least a portion of said receiving layer to at least a portion of said activating layer when placed in contact.

24. The method of claim 23, wherein applying said adhesive means comprises rendering an adhesive layer onto at least a portion of at least one of said receiving layer or said activating layer.

25. The method of claim 23, wherein applying said adhesive means comprises incorporating one or more adhesive materials into at least one of said receiving layer or said activating layer.

26. The method of claim 22, wherein said receiving layer further comprises one or more polymers that function together with said one or more deactivators to cause and maintain said one or more masking colorants to be in said initial colored state.

27. The method of claim 22, wherein at least one of said activating layer or said receiving layer further comprises one or more static colorants that are capable of being visually observed upon at least a portion of said one or more masking colorants of said receiving layer being partially or fully in said final colorless state.

28. The method of claim 22, further comprising rendering a colorant layer disposed onto at least a portion of said activating layer, wherein said colorant layer comprises one or more static colorants that are capable of being visually observed upon at least a portion of said one or more masking colorants of said receiving layer being partially or fully in said final colorless state.

29. The method of claim 22, further comprising rendering a colorant layer disposed onto at least a portion of said receiving layer, wherein said colorant layer comprises one or more static colorants that are capable of being visually observed upon at least a portion of said one or more masking colorants of said receiving layer being partially or fully in said final colorless state.

30. The method of claim 22, further comprising applying a timing layer disposed onto at least a portion of said activating layer, wherein said timing layer at least partially retards the rate of migration of said one or more migratory activators into said receiving layer.

31. The method of claim 22, further comprising applying a timing layer disposed onto at least a portion of said receiving layer, wherein said timing layer at least partially retards the rate of migration of said one or more migratory activators into said receiving layer.

32. The method of claim 22, further comprising rendering one or more base substrates, wherein at least a portion of at least one of said activating layer or said receiving layer is disposed onto said one or more base substrates.

33. The method of claim 32, wherein one of said one or more base substrates comprises an indicia area that is capable of being visually observed upon at least a portion of said one or more masking colorants of said receiving layer being partially or fully in said final colorless state.

34. The method of claim 22, wherein the leuco dye is a spiropyran, benzopyran, fluoran dye, phthalide dye, triarylmethane phthalide, diarylmethane phthalide, or monoheterocyclic substituted phthalide.

35. The method of claim 34, wherein said fluoran dye is 2'-anilino-3'-methyl-6'-(dibutylamino) fluoran.

36. The method of claim 35, wherein said fluoran dye is 2'-anilino-3'-methyl-6'-(dibutylamino) fluoran.

37. The method of claim 35, wherein said phthalide dye is crystal violet lactone.

38. The method of claim 34, wherein said phthalide dye is crystal violet lactone.

39. The method of claim 34, wherein the leuco dye is a spiropyran, benzopyran, fluoran dye, phthalide dye, triarylmethane phthalide, diarylmethane phthalide, or monoheterocyclic substituted phthalide.

40. The method of claim 22, wherein the one or more electron accepting compounds are Lewis acids, clays, or proton-donating compounds.

41. The method of claim 22, wherein the one or more electron accepting compounds are malonic acid, maleic acid, malic acid, fumaric acid, terephthalic acid, or propyl gallate.

42. The method of claim 22, wherein said one or more masking colorants are one or more leuco dyes.

43. A method for indicating a predetermined time period has elapsed, said method comprising:
   providing a time validation indicator that comprises,
      a receiving layer comprising:
         (i) one or more masking colorants; and
         (ii) one or more deactivators that cause and maintain said one or more masking colorants to be in an initial colored state, wherein the one or more deactivators are one or more electron accepting compounds; and
      an activating layer comprising one or more migratory activators that migrate into said receiving layer to cause at least a portion of said one or more masking colorants to advance to a final colorless state that results in a visual color change of said receiving layer;

placing at least a portion of said receiving layer in contact with at least a portion of said activating layer to initiate the predetermined time period and the migration of said one or more migratory activators into said receiving layer; and detecting said visual color change of said receiving layer that indicates the predetermined time period has elapsed.

44. The method of claim 43, further comprising applying said time validation indicator to at least a portion of a surface of an object.

45. The method of claim 43, wherein said time validation indicator further comprises an adhesive means that bonds together at least a portion of said receiving layer with at least a portion of said activating layer when placed in contact.

46. The method claim 43, wherein said receiving layer further comprises one or more polymers that function together with said one or more deactivators to cause and maintain said one or more masking colorants to be in said initial colored state.

47. The method of claim 43, wherein at least one of said activating layer or said receiving layer further comprises one or more static colorants that are capable of being visually observed upon at least a portion of said one or more masking colorants of said receiving layer being partially or fully in said final colorless state.

48. The method of claim 43, wherein said time validation indicator further comprises a colorant layer having one or more static colorants that are capable of being visually observed upon at least a portion of said one or more masking colorants of said receiving layer being partially or fully in said final colorless state.

49. The method of claim 43, wherein said time validation indicator further comprises a timing layer that at least partially retards the rate of migration of said one or more migratory activators into said receiving layer.

50. The method of claim 43, wherein said time validation indicator further comprises one or more base substrates.

51. The method of claim 50, wherein one of said one or more base substrates comprises an indicia area that is capable of being visually observed upon at least a portion of said one or more masking colorants of said receiving layer being partially or fully in said final colorless state.

52. The method of claim 43, wherein the one or more electron accepting compounds are Lewis acids, clays, or proton-donating compounds.

53. The method of claim 43, wherein the one or more electron accepting compounds are malonic acid, maleic acid, malic acid, fumaric acid, terephthalic acid, or propyl gallate.

* * * * *